United States Patent [19]

Tesei et al.

[11] 4,006,198
[45] Feb. 1, 1977

[54] METHOD FOR THE PREPARATION OF TERTIARY OLEFINS

[75] Inventors: Renato Tesei; Vittorio Fattore; Franco Buonomo, all of San Donato Milanese, Italy

[73] Assignee: Snam Progetti, S.p.A., San Donato Milanese, Italy

[22] Filed: Aug. 1, 1975

[21] Appl. No.: 601,207

[30] Foreign Application Priority Data

Aug. 2, 1974 Italy .................................. 25938/74

[52] U.S. Cl. ............................ 260/682; 260/632 B
[51] Int. Cl.² ....................... C07C 1/00; C07C 1/24
[58] Field of Search ........................ 260/682, 632 B

[56] References Cited

UNITED STATES PATENTS

| | | | |
|---|---|---|---|
| 2,468,764 | 5/1949 | Laurent | 260/682 |
| 2,636,057 | 4/1953 | Cutcher et al. | 260/682 |

FOREIGN PATENTS OR APPLICATIONS

| | | | |
|---|---|---|---|
| 1,165,479 | 10/1969 | United Kingdom | 260/682 |
| 1,233,020 | 5/1971 | United Kingdom | 260/682 |
| 1,173,128 | 12/1969 | United Kingdom | 260/682 |

*Primary Examiner*—Patrick P. Garvin
*Assistant Examiner*—John F. Niebling
*Attorney, Agent, or Firm*—Ralph M. Watson

[57] ABSTRACT

A method is disclosed for preparing tertiary olefins starting from the corresponding tertiary ethers, the improvement consisting in contacting the ether with a catalyst composed by active alumina modified by reaction with a silicon compound selected among those corresponding to the general formula:

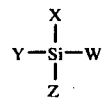

wherein X,Y,Z and W can be —R, —OR, —Cl, —Br, —SiH₃, —COOR, —Sih$_n$O$_m$, R being hydrogen, an alkyl, cycloalkyl, aryl, aralkyl or alkyl-cycloalkyl radical of from 1 to 30 carbon atoms, n and m being integers comprised between 1 and 3. The advantages afforded by the invention are mainly the nearly quantitative yields and the high purity of the end products.

12 Claims, No Drawings

METHOD FOR THE PREPARATION OF TERTIARY OLEFINS

This invention relates to a method for the preparation of pure tertiary olefins, starting from the corresponding tertiary ethers.

It is known that, by reacting a low-molecular-weight alcohol with a mixture of olefins only the ter-alkyl ethers are obtained since the secondary olefins react very slowly and the primary olefins are completely inert.

It is now been found that it is possible to prepare the pure tertiary olefin with a high yield starting from the aforementioned ter-alkyl ethers by contacting the ether with a particular catalyst system, the ether being decomposed into the olefin and the corresponding low-molecular weight alcohol which can be recycled and reacted with an olefin mixture again.

The tertiary olefins are highly appreciable starting materials for the preparation of polymers and chemicals and it is thus extremely important to be capable of isolating them in the purest possible form.

Methods for the obtaining tertiary olefins are known. For example, a few of them are based on the use of $H_2SO_4$, which, however, in addition to having a corrosive action, has several drawbacks among which the necessity of concentrating the acid prior to recycling. Other methods are based on the decomposition of the corresponding methyl ethers in the presence of appropriate catalyst systems.

However, the use of the catalysts as mentioned above for the reaction aforementioned, causes, in the majority of the cases, the formation of dialkylethers as a result of the dehydration of the corresponding primary alcohols.

Such a reaction takes place the more easily, the higher is the working temperature, a few conventional catalysts requiring the adoption of comparatively high temperatures, that which involves a loss of alcohol with the consequential necessity of feeding it fresh alcohol to the initial etherification reaction.

Furthermore, the formation of a dialkyl ether requires a greater complexity of the installation since a separation of the dialkyl ether from the tertiary olefin becomes necessary. Still more, the formation of a considerable amount of dialkyl ether also requires the dehydration of the primary alcohol prior to the recycling thereof, otherwise in the etherification reaction there would be a demixing of the phases along with the possibility of tertiary alcohol formation.

Another defect experienced when the reaction is carried out beyond certain temperature levels is given by the occurrence of dimerization and trimerization of the tertiary olefin as recovered from the decomposition of the ethers.

The foregoing and other defects are done away with, according to the present invention, when the decomposition reaction of the ter-alkyl ethers is carried out in the presence of a catalyst system composed by active aluminas modified by the partial substitution of superficial —OH units by silanolic units according to what has been disclosed in copending application Serial No. 519,792, filed October 31, 1974 in the name of the same Applicant.

According to said patent application, it is possible to improve the physical properties of the materials which are composed by metal oxides by treating the latter with a silicon compound and subjecting the product thus obtained to drying and to a controlled oxidation.

The silicon compounds which can be used correspond to the general formula:

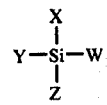

wherein X, Y, Z and W can be —R, —OR, —Cl, —Br, —SiH$_3$, —COOR, —SiH$_n$Cl$_n$, R being hydrogen, an alkyl radical, a cycloalkyl radical, an aryl radical, an alkyl-aromatic radical or an alkyl cycloalkyl radical having from 1 to 30 carbon atoms, such as for example methyl, ethyl, isopropyl, n-propyl, n-butyl, isobutyl, cyclohexyl, cyclopentyl, phenyl, phenylcyclohexyl, alkylphenyl, n and m being integers comprised between 1 and 3.

Among the compounds indicated above the esters of the orthosilicic acid are preferred such as: methyl, ethyl, propyl, isopropyl, isobutyl and nor-butyl tetrasilicates.

In the case of alumina, especially the gamma and eta ones, the applicant has found, and this is the subject matter of the present invention, that alumina, when treated as specified above, it originates a catalyst adapted to the reaction of decomposition of the ter-alkyl ethers to give tertiary olefins of a high purity without the above indicated defects as exhibited by the catalysts as used heretofore for this reaction.

The amount of silanolic groups bound to the alumina surface varies from 1% to 20%, preferably from 3% to 8%, by weight.

The reaction of decomposition of the ter-alkyl ethers takes place with good yields still under atmospherical pressures, but it is preferred to operate under slightly superatmospheric pressures so as to permit the use of cooling water without any other expedient to carry out the condensation of the products which are obtained.

The working pressures are generally ranging from 1 to 10 kilograms/sq.cm/; preferably under a pressure which is at least equal to the vapour pressure of the described olefin at the condensation temperature which is foreseen.

The reaction is carried out at a temperature below 250° C, in the range 100°–250° C and preferably in the range from 130° to 230° C. The reaction is carried out at a spatial velocity, as expressed in terms of volume of liquid per volume or catalyst an hour (LHSV) ranging between 0.5 and 30, and preferably in the range 1 to 5.

The primary alcohols which can be recovered on completion of the decomposition run according to the invention preferably contain from 1 to 6 carbon atoms.

The method according to the present invention can be employed for the recovery of tertiary olefins from mixtures of C$_4$ to C$_7$ olefins, such as, for example, those coming from the thermic cracking, steam cracking or catalyst cracking.

Among the several tertiary olefins which can be obtained in a pure state there can be listed isobutylene, isoamylenes such as 2-methyl-2-butene and 2-methyl-1-butene, the isohexenes such as 2-3, dimethyl-1-butene, 2-3-dimethyl-2-butene, 2-methyl-1-pentene, 2-methyl-2-pentene, 3-methyl-2-pentene (cis and trans), 2-ethyl-1-butene and 1-methyl-cyclopentene, or, lastly, the tertiary isoheptenes.

The conversion of the ter-alkyl ether into primary alcohol and tertiary olefin is virtually quantitative. No formation is experienced of dimers and trimers of the recovered tertiary olefin and no tertiary alcohol is likewise formed.

The working procedures and the advantages of the method according to the invention will become clearer from the scrutiny of the ensuing illustrative examples which in no wise should be construed as limiting the invention.

EXAMPLE 1

Spheroidal gamma-$Al_2O_3$ is prepared according to the method disclosed in U.S. Pat. No. 3,416,888 by the same Applicant Company.

It consists in dripping into a mineral oil of the water immiscible type, kept at 90° C, a mixture of ammonium acetate, aluminium chlorohydroxide and an appropriate gelling agent. On the bottom of the column gel spherules are collected which, properly treated with $NH_3$, washed with $H_2O$, crystalline as an alpha-monohydrate. The dried and subsequently fired spherules are converted into gamma-$Al_2O_3$.

100 grams of thusly prepared gamma-$Al_2O_3$ are immersed in 200 cubic centimeters of $(C_2H_5O)_4Si$ (ethyl orthosilicate) and kept into contact with the liquid during one hour at a temperature of 60° C. On completion the solid is separated from the excess liquid and transferred into a quartz tube which is immersed in a small electric oven. A stream of $N_2$ is fed in and the mass is heated slowly until reaching the boiling point temperature of tetraethyl silicate (160°– 180° C); by so doing the unreacted silicate is completely distilled.

The heat treatment is continued up to 600° C: at this temperature the flow of $N_2$ is discontinued and air is fed in.

The product which is obtained is a gamma-$Al_2O_3$ which contains 6.1% of $SiO_2$ in the form of ≡SiOH groups bonded to the surface of the gamma-$Al_2O_3$ by siloxane bridges

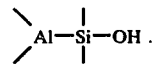

The chemical specifications of a thusly modified gamma-$Al_2O_3$ are:

| | | |
|---|---|---|
| — | Surface area | 220 square meters per gram |
| — | Overall porosity | 0.92 cu.cms.per gram |
| — | Packing density (PBD) | 0.48 grs/cu.cm. |

EXAMPLE 2

A pelletized and spheroidal gamma-$Al_2O_3$ is prepared according to the procedures disclosed in the following: on a rotary plate, which is sloping 45° with respect to the horizontal plane, finely powdered gamma-$Al_2O_3$ is placed and during the rotation of the plate where is sprayed on the powder a 0.1% aqueous solution of methocel (hydrated methylcellulose). Spheroidal cores are formed the size of which is governed by the time of stay of same on the plate and the amount of powder which lies on the plate.

Once the desired size has been attained, the alumina is dried during 24 hours at 120° C and then fired in air at 500° C.

A sample of gamma-$Al_2O_3$ thusly prepared undergoes the same treatment as disclosed in Example 1 up to the heating in $N_2$ stream at 180° C.

At this stage a steam stream is sent onto the sample until achieving a complete hydrolysis of the —O—$C_2H_5$ groups bonded to silicon, which is bound, in turn, to alumina through an oxygen bridge. When the effluent does not show any trace of $C_2H_5OH$, the heat treatment is resumed again in an air stream up to 500° C.

Also in this case a gamma-$Al_2O_3$ is obtained, which contains 6.5% of $SiO_2$ in the form of ≡Si-OH groups bonded to the surface of the gamma-$Al_2O_3$.

The chemical and physical specification of the thusly modified gamma-$Al_2O_3$ are:

| | | |
|---|---|---|
| — | Surface area | 265 sq.meters/gram |
| — | Overall porosity | 0.88 cu.cm/gram |
| — | Packing density (PBD) | 0.51 grs/cu.cm |

EXAMPLES 3, 4, 5, 6, 7 and 8

These are concerned with the decomposition of the methyl-terbutyl ether. The reaction has been carried out in a tubular reaction having an inside diameter of 20 mms. containing 80 cu.cms of a spheroidal catalyst according to the invention having a grit size comprised between 5 and 8 mesh, A.S.T.M. USA Series.

In the Examples 3, 4, 5, 6 there has been used the catalyst containing 6.1% by weight of $SiO_2$, as prepared according to Example 1.

In Examples 7 and 8, conversely, there has been used the catalyst containing 6.5% by weight of $SiO_2$ as prepared according to Example 2.

The charge, introduced in the reactor by means of a metering pump, was heated at the specified temperature by causing it to pass through a preheating tube having an inside diameter of 4 mms. and the length of one meter.

The temperature of the preheater and that of the reactor were controlled by a thermostatic bath containing silicone oil.

Downstream of the reactor there were arranged a pressure control valve adjusted at 6 kgs/sq.cm and a product collection system cooled with dry ice.

The feeding of the charge was 40 cu.cms an hour, corresponding to a spatial velocity (LHSV) of 0.5.

The temperature of the bath in which the reactor was immersed in Examples 3, 4, 5, 6 was 160°, 180°, 200°, 205° C, respectively. In the Examples 7 and 8 the same temperature has been adopted as in the Examples 3 and 4, that is, 160° and 180° C.

The results which have been obtained are tabulated in Table 1.

TABLE 1

| Example No. | %SiO₂ in the silanized catalyst | Spatial velocity (LHSV) | Pressure kg/sq.cm | Temperature °C | Ether conversion % | Methanal recovery % | Isobutylene recovery % |
|---|---|---|---|---|---|---|---|
| 3 | 6,1 | 0,5 | 6 | 160 | 76 | 98,5 | 100 |
| 4 | | | | 180 | 91 | 95 | 100 |
| 5 | | | | 200 | 95 | 91 | 98 |
| 6 | | | | 205 | 98 | 77 | 95 |
| 7 | 6,5 | | | 160 | 76 | 98 | 100 |
| 8 | | | | 180 | 90,5 | 95 | 100 |

On comparing Example 3 with Example 7 and Example 4 with Example 8 it can be seen that it is indifferent to use the catalyst prepared according to Example 1 or that prepared according to Example 2 in that they virtually produce the same results.

EXAMPLES 9, 10, 11, 12, 13

These are concerned with the decomposition reaction of the methyl ter.butyl ether which has been carried out by using the same apparatus of the preceding Examples and by working with the catalyst of Examples 3, 4, 5 and 6 and under the same pressure of 6 kgs/sq.cm. The only difference was the charge feeding which was 80 cu.cms. an hour, corresponding to a spatial velocity of 1 (LHSV).

In these Examples only the temperature has been varied and, more exactly, the temperature of the bath in which the reactor was immersed was 160°, 170°, 180°, 195°, 210° C, respectively.

The results which have been obtained are tabulated in Table 2.

TABLE 2

| Example No. | Spatial velocity (LHSV) | Pressure kg/sq.cm. | Temperature °C | Ether conversion % | Methanol recovery % | Isobutylene recovery % |
|---|---|---|---|---|---|---|
| 9 | 1 | 6 | 160 | 71 | over 99 | 100 |
| 10 | | | 170 | 82,5 | 98 | 100 |
| 11 | | | 180 | 92,5 | 96 | 100 |
| 12 | | | 195 | 94,5 | 93 | 99 |
| 13 | | | 210 | 98 | 80 | 97,5 |

As can be seen in the results of Examples 3 and 9, by operating with spatial velocities of 0.5 and 1, respectively, and at the external temperature of 160° C, there are obtained internal conversions of 70% − 75% whereas the recoveries of methanol and isobutylene are virtually quantitative.

By operating under these conditions in an industrial installation, the unconverted hexene, after recovery of methanol and isobutylene, can be recycled to the decomposition reactor, with the advantage of nearly completely preventing the formation of by-products, more particularly dimethyl ether.

By bringing the temperature above 160° C to about 180° C, the conversion of methyl ter.butyl ether is increased, without the formation of high amounts of dimethyl ether. The recovery of isobutylene is still virtually quantitative also at these temperatures.

EXAMPLES 14, 15, 16

These are concerned with the decomposition reaction of methyl ter.butyl ether which has been carried out in the same apparatus, under the same pressure of 6 kgs/sq.cm and using the same catalyst as in Examples 3, 4, 5, 6 with the difference that the charge feed on was 160 cu.cms an hour, corresponding to a spatial velocity (LHSV) of 2.

In these Examples only the temperature has been varied of the bath in which the reactor was immersed, by operating at 195°, 205°, 220° C, respectively. The results which have been obtained are tabulated in

TABLE 3

| Ex. No. | Spatial velocity (LHSV) | Pressure kgs/sq.cm. | Temper. °C | Ether conver. % | Methanol recovery % | Isobutylene recovery % |
|---|---|---|---|---|---|---|
| 14 | 2 | 6 | 195 | 85 | 97,5 | 100 |
| 15 | | | 205 | 94 | 96 | 98,5 |
| 16 | | | 220 | 98 | 86 | 97,5 |

EXAMPLES 17, 18, 19

These Examples are concerned with the decomposition reaction of methyl-ter.butyl ether, which has been carried out in the same apparatus, under the same pressure of 6 kgs/sq.cm and using the same catalyst as in Examples 3, 4, 5, 6 with the difference that the charge feed was 240 cu.cms. an hour, corresponding to a spatial velocity (LHSV) of 3.

In these Examples only the temperatures has been varied of the bath in which the reactor was immersed, operating at 200°, 220°, 230° C, respectively.

The results which have been obtained are tabulated in

TABLE 4

| Ex. No. | Spatial velocity | Pressure kgs/sq. cm | Temper. °C | Ether conver. % | Methanol recovery % | Isobutylene recovery % |
| --- | --- | --- | --- | --- | --- | --- |
| 17 | 3 | 6 | 200 | 84 | 97 | 100 |
| 19 |   |   | 220 | 95 | 96 | 100 |
| 19 |   |   | 230 | 98 | 92 | 99 |

By comparing Examples 5, 12, 15 and 18, in which there has been obtained the same ether conversion of 94–95%, it is noted, at a spatial velocity 2 and 3, an improvement of the relativity with respect to the methanol recovery which from 91% rises to 93% and to 96%.

A similar behaviour can be seen by comparing Examples 6, 13, 16 and 19, in which there has been obtained the same ether conversion of 98%. The methanol recovery, in fact, rises to 77%–80% at the spatial velocities of 0.5 and 1, and to 86% at the spatial velocity of 2 and to 92% at the spatial velocity of 3.

The isobutylene recovery, which already was high, becomes nearly quantitative as the spatial velocity is increased from 0.5 to 3.

EXAMPLE 20

This Example has been performed by operating with the same apparatus, the same catalyst and under the same pressure of 6 kilograms/sq.cm as in Examples 3, 4, 5 and 6, by varying, however, the charge and exactly by using methyl-ter-amyl ether.

The charge feed was 80 cu.cms. an hour, corresponding to a spatial velocity (LHSV) of 1.

By operating with a temperature of the external bath of 180° C, an ether conversion of 99% has been obtained, with a methanol recovery at 96% and an isoamylene recovery over 99%.

By comparing these results with those of Example 13 as obtained starting from methyl-ter-butyl ether at the same spatial velocity, it is noted that the decomposition of methyl-ter-amyl ether takes place at a lower temperature (180° instead of 210° C) and consequently, the conversion of the charged in ether being equal (98%–99%), it is possible to have a much higher recovery of methanol (96% instead of 80%) and also a higher recovery of tertiary olefin (over 99% of isoamylenes instead of 97.5% of isobutylene).

EXAMPLES 21, 22, 23

These have been carried out with the same apparatus, and under the same pressure of the preceding Examples. The catalyst was composed by 80 cu.cms. of catalysts prepared according to Example 1 of this invention and containing $SiO_2$ in an amount of 1.2% in Example 21, 2.6% in Example 22 and 10% in Example 23, respectively. As the charge, methyl-ter-butyl ether has been used and its feed was 80 cu.cms an hour, corresponding to a spatial velocity (LHSV) of 1. The temperature of the external bath was still 180° C.

The results which have been obtained are tabulated in Table 5.

TABLE 5

| Example No. | %$SiO_2$ in catalyst | Outside temper. °C | Spatial velocity (LHSV) | Pressure kgs/sq.cm | Ether conver. % | Methanol recovery % | Isobutylene recovery % |
| --- | --- | --- | --- | --- | --- | --- | --- |
| 21 | 1,5 | 180 | 1 | 6 | 50 | 97 | 100 |
| 22 | 3 | 180 | 1 | 6 | 71 | 95 | 100 |
| 23 | 10 | 180 | 1 | 6 | 93 | 90 | 82 |

These results show that the contents of $SiO_2$ in the silanized catalyst can be widely varied.

With the catalyst containing 10% of $SiO_2$ at the temperature of 180° C there is a decrease in the recovery of isobutylene.

By comparing these results with those of Example 11, carried out at the same temperature with the silanized catalyst of the present invention which contains 6.1% of $SiO_2$, it is seen that, the other conditions being the same, the catalyst which affords the most satisfactory results is the one containing 6.1% of $SiO_2$, the follow those containing an amount of $SiO_2$ of 3.0%, 1.5% and 10% by weight, respectively.

EXAMPLES 24 and 25

There have been carried out, by using the same temperature as in the preceding Examples, two tests in which, instead of the catalyst of the present invention, there have been used for comparison purposes 80 cu.cms. of a spheroidical gamma-alumina having a grit size comprised between 5 and 8 mesh A.S.T.M.-U.S.A., a surface area of 264 sq. meters per gram, an overall porosity of 0.88 cu. cms/grams and a PBD of 0.52 grams/cu/cm. The charge was formed by methyl-ter-butyl ether which was fed in at a rate of flow of 80 cu.cms. an hour, corresponding to a spatial velocity (LHSV) of 1. The pressure was 6 kgs.sq.cm. The temperature of the external bath was 200° C in Example 24 and 230° C in Example 25.

The results which have been obtained are tabulated in Table 6.

TABLE 6

| Example No. | Catalyst | External temper. | Spatial velocity (LHSV) | Pressure kgs/sq. cm. | Ether conver. % | Methanol recovery % | Isobutylene recovery % |
| --- | --- | --- | --- | --- | --- | --- | --- |
| 24 | gamma-alumina | 200° C | 1 | 6 | 29 | 78 | 99 |
| 25 | gamma-alumina | 230° C | 1 | 6 | 70 | 63 | 100 |

In these Examples the considerable difference can be appreciated, which exists between the catalyst of the present invention and gamma-alumina.

By comparing the results of Example 24 with those of Example 13, it can be seen that, the methanol recovery being the same (78% and 80%), the decomposition of the ether is 98% with the catalyst according to the present invention, whereas a decomposition of ether as low as 29% is obtained with gamma-alumina.

From the results of Example 25, as compared with those of Example 9, it can be seen that, the ether conversion being the same (70% and 71%) the recovery of the methanol is more than 99% with the catalyst according to the present invention, whereas with the gamma-alumina the recovery of methanol is as low as 63% only.

EXAMPLES 26 and 27

Two tests have been carried out, using the same apparatus of the preceding Examples, and in such tests there have been used, for comparison purposes, 80 cu.cms of silica and commercial silica-alumina (87% – 13% by weight), both in the form of small cylinders.

The charge was composed by methyl-ter-butylene ether which was fed at a rate of flow of 80 cu.cms an hour, corresponding to a spatial velocity (LHSV) of 1.

The temperature of the external bath was still 180° C, the pressure 6 kgs/sq.cm.

The results which have been obtained are tabulated in Table 7.

TABLE 7

| Example No. | Catalyst | External temper. °C | Spatial velocity (LHSV) | Pressure kgs/sq.cm. | Ether conver. % | Methanol recovery % | Isobutylene recovery % |
|---|---|---|---|---|---|---|---|
| 26 | silica | 180 | 1 | 6 | 1 | — | — |
| 27 | silica-alumina 87%–13% | 180 | 1 | 6 | 95 | 90 | 73 |

By comparing these results with those of Example 11, carried out under the same conditions with silanized alumina containing 6.1% of $SiO_2$, it can be seen that with this catalyst, according to the present invention, the results are considerably improved. As a matter of fact, in Example 11 there is an ether conversion of 92.5% with a methanol and isobutylene recovery of 96% and over 99%, whereas with silica (Example 26) there is no conversion in practice whereas with silica-alumina (Example 27) the conversion is high (95%) but the recovery of methanol and, above all, of isobutylene are considerably lowered.

What is claimed is:

1. A method for the preparation of tertiary olefins starting from the corresponding tertiary ethers, consisting in contacting the ether with a catalyst compound by active alumina obtained by reacting alumina with a silicon compound selected among those corresponding to the following formula:

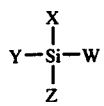

wherein X,Y,Z and W can be —R,—OR, —Cl, —Br, —SiH$_3$, —COOR, —SiH$_n$Cl$_m$ R being hydrogen, an alkyl, cocloalkyl, aryl, aralkyl, or alkyl-cycloalkyl radicals having from 1 to 30 carbon atoms, n and m being integers comprised between 1 and 3 and thereafter drying and subjecting the reacted alumina to controlled oxidation.

2. A method for the preparation of tertiary olefins according to claim 1, characterized in that the catalyst is composed of active alumina containing silanol groups bound to the alumina in an amount variable from 1 to 20% by weight.

3. A method for preparation of tertiary olefins according to claim 1, characterized in that the reaction is carried out at temperatures comprised between 100° and 250° C.

4. A method for the preparation of tertiary olefins according to claim 1, characterized in that the reaction is carried out under pressures which vary from 1 to 10 kilograms per square centimeter.

5. A method for the preparation of tertiary olefins according to claim 1, characterized in that the reaction is carried out under a pressure equal to the vapour pressure of said tertiary olefin at the condensation temperature.

6. A method for the preparation of tertiary olefins according to claim 1, characterized in that the reaction is carried out at a spatial velocity comprised between 0.5 and 30.

7. A method for the preparation of tertiary olefins according to claim 1, characterized in that the reaction is carried out starting from ter-alkyl ethers composed of low-molecular-weight -OR groups selected from those having a number of carbon atoms variable from 1 to 6 and by a tertiary hydrocarbonaceous radical derived from an olefin selected from those having a number of carbon atoms variable from 4 to 7.

8. A method for the preparation of tertiary olefins according to claim 1, characterized in that the catalyst is composed of active alumina in an amount variable from 3% to 8% by weight.

9. A method for the preparation of tertiary olefins according to claim 1, characterized in that the reaction is carried out at temperatures comprised between 130° and 230° C.

10. A method for preparation of tertiary olefins according to claim 1, characterized in that the reaction is carried out at a spatial velocity comprised between 1 and 5.

11. A method for the preparation of tertiary olefins according to claim 1, wherein X,Y,Z and W are methyl, ethyl, isopropyl, n-propyl, n-butyl, isobutyl, cyclohexyl, cyclopentyl, phenyl, phenylcyclohexyl, and alkylphenyl.

12. A method for the preparation of tertiary olefins starting from the corresponding tertiary ethers consisting essentially of contacting said tertiary ether at a temperature of from 100° to 250° C, with a catalyst composed of active alumina obtained by contacting gamma or eta alumina with a sufficient amount of ethyl orthosilicate to add from 1% to 20% by weight of silanolic groups that are bound to the surface of said gamma or eta alumina by drying the mixture of said gamma or eta alumina and ethyl orthosilicate and subjecting the dried product to controlled oxidation, to form said tertiary olefin.

* * * * *

UNITED STATES PATENT AND TRADEMARK OFFICE
CERTIFICATE OF CORRECTION

PATENT NO. : 4,006,198
DATED : February 1, 1977
INVENTOR(S) : Renato Tesei, et al It is certified that error appears in the above-identified patent and that said Letters Patent are hereby corrected as shown below:

Col. 3, line 23, correct "crystalline" to read --crystallize--;

line 68, correct "where" to read -- there --.

Cols. 5 and 6, Table 1, 7th heading, correct "Methanal" to read -- Methanol --.

Signed and Sealed this

Thirteenth Day of September 1977

[SEAL]

Attest:

RUTH C. MASON
Attesting Officer

LUTRELLE F. PARKER
Acting Commissioner of Patents and Trademarks